United States Patent [19]

Takiguchi

[11] Patent Number: 4,857,748
[45] Date of Patent: Aug. 15, 1989

[54] APPARATUS FOR OPTICALLY MEASURING THE THREE-DIMENSIONAL SURFACE SHAPE AND INNER STRUCTURE OF AN OBJECT

[75] Inventor: Yoshihiro Takiguchi, Shizuoka, Japan

[73] Assignee: Hamamatsu Photonics Kabushiki Kaisha, Shizuoka, Japan

[21] Appl. No.: 74,879

[22] Filed: Jul. 17, 1987

[30] Foreign Application Priority Data

Jul. 18, 1986 [JP] Japan .................. 61-170654

[51] Int. Cl.$^4$ ........................... G01N 21/86
[52] U.S. Cl. .................. 250/560; 250/213 VT; 356/376
[58] Field of Search ............... 250/213 VT, 368, 227, 250/560, 561; 356/375, 376, 379, 380

[56] References Cited

U.S. PATENT DOCUMENTS

| | | | |
|---|---|---|---|
| 3,865,493 | 2/1975 | Morton ......................... | 356/380 |
| 4,238,148 | 12/1980 | Courtney-Pratt . | |
| 4,293,221 | 10/1981 | Kay et al. ..................... | 356/318 |
| 4,417,274 | 11/1983 | Henry .......................... | 356/380 |
| 4,542,290 | 9/1985 | Tan et al. ..................... | 250/213 VT |

OTHER PUBLICATIONS

Richard Lear, "Fast Imaging Applications in the Nuclear Test Program", 2/84; pp. 497–503.
H. R. Taylor, "Recording Flash X-Ray Burst Times with Scintillation Crystals," 11/71; pp. 1627–1629.
L. G. Cohen, "Interferometric Measurements of Minimum Dispersion Spectra in Short Lengths of Single-Mode Fibre".
A. Barthelemy, "New Method for Precise Characterization of Multimode Optical Fibers," Mar. 18, 1982; pp. 247–250.

Primary Examiner—David C. Nelms
Assistant Examiner—Eric F. Chatmon
Attorney, Agent, or Firm—Finnegan, Henderson, Farabow, Garrett & Dunner

[57] ABSTRACT

An apparatus for optically measuring a three-dimensional surface shape and inner structure of a three-dimensional object without destruction of the object. When a light pulse having a short pulse width is applied to the object, there are observed a flux of light pulses reflected from or transmitted through the object which has information on the three-dimensional surface shape and inner structure of the object. This apparatus optically measures and analyzes in the order of a picosecond the intensity distribution of the light pulses from the object with time and space, to thereby obtain a complete three-dimensional image of the object.

17 Claims, 5 Drawing Sheets

APPARATUS FOR OPTICALLY MEASURING THE THREE-DIMENSIONAL SURFACE SHAPE AND INNER STRUCTURE OF AN OBJECT

BACKGROUND OF THE INVENTION

1. Field of the Invention

The present invention relates to an apparatus for the three-dimensional measurement of a surface shape and inner structure of an object to be measured, and more particularly to a three-dimensionally measuring apparatus by which the three-dimensional surface shape and inner structure of a three-dimensional object can be optically measured without requiring the destruction of the object.

2. Prior Art

An endoscope is known as one apparatus for observing inner parts of an object. Further, there has been proposed an apparatus using light for measuring the three-dimensional surface shape of an object.

In a case where the endoscope is employed in the measurement of the structure of an object, a surface shape of the object can be observed to some extent, but a three-dimensional inner structure of an object is observed by measuring light transmitted through the object, the intensity of the light transmitted through the object depends on the transmittance and thickness of the object. Accordingly, unless the object is very thin, no image of the transmitted light can be attained.

SUMMARY OF THE INVENTION

When a pulse of light is applied to the surface of an object, light reflected from the object and light transmitted through the object can be observed. Both the reflected and transmitted light pulses include light pulses scattered within the interior of the object, which are time-delayed depending on the inner structure of the object.

This invention is based on the technical concept that by detecting the reflected or transmitted light pulses including the scattered light pulses and analyzing the time-delayed distribution thereof, a three-dimensional surface shape and inner structure of an object can be measured.

It is therefore an object of the present invention to provide a three-dimensionally measuring apparatus for optically measuring a three-dimensional surface shape and inner structure of an object, where the three-dimensional shape and inner structure of the object can be optically measured without requiring the destruction of the object.

To attain the foregoing object of the invention, according to a first embodiment of the invention there is provided a three-dimensionally measuring apparatus for optically measuring a three-dimensional surface shape and inner structure of an object to be measured, which comprises a pulse light source for generating pulsed light having a short pulse width. Light conducting means are also provided for guiding the pulsed light from the pulse light source to the object. An optical system focuses the light reflected from the object and ultrahigh speed detecting means detect the focused light and measure the change of the intensity thereof with respect to time and space. Finally, analyzing means are provided for analyzing an output of the ultrahigh speed light detecting means.

According to a second embodiment of the invention, the three-dimensionally measuring apparatus comprises a pulse light source for generating pulsed light having a short pulse width and ultrahigh speed light detecting means. Light conducting means guide the pulsed light from the pulse light source to the interior of the object and an optical system focuses the light transmitted through the interior of the object onto an input portion of the ultrahigh speed light detecting means. Analyzing means for analyzing an output of the ultrahigh speed light detecting means are also provided.

According to a third embodiment of the invention, the three-dimensionally measuring apparatus comprises a pulse light source for generating pulsed light having a short pulse width and ultrahigh speed light detecting means. An optical system irradiates the object from the outside to the inside with the pulsed light from the pulse light source. An optical image fiber having one end thereof introduced into the inside of the object transmits a light image of the pulsed light and another optical system focuses an output image of the image fiber onto an input portion of ultrahigh speed light detecting means. Analyzing means then analyze an output of the ultrahigh speed light detecting means.

According to a fourth embodiment of the invention, the three-dimensionally measuring apparatus comprises a pulse light source for generating pulsed light having a short pulse width and ultrahigh speed light detecting means. Light conducting means guide the pulsed light from the pulse light source into the inside of the object. An optical image fiber having one end thereof introduced into the inside of the object transmits an image of light reflected from the inside of the object after being projected into the object from the light conducting means. An optical system focuses the output image of the image fiber onto an input portion of the ultrahigh speed light detecting means and analyzing means analyze an output of the ultrahigh speed light detecting means.

According to a fifth embodiment of the invention, the three-dimensionally measuring apparatus comprises a pulse light source for generating pulsed light having a short pulse width and ultrahigh speed light detecting means. An optical image fiber has one end thereof introduced into the inside of the object and an optical system guides the pulsed light from the pulse light source into the optical image fiber. Another optical system focuses an image of light from the optical image fiber, after being radiated into and reflected from the inside of the object, onto an input portion of the ultrahigh speed light detecting means. Analyzing means analyze an output of the ultrahigh speed light detecting means.

DETAILED DESCRIPTION OF THE PREFERRED EMBODIMENT

The present invention will be described in more detail with reference to the accompanying drawings.

Figure 1:
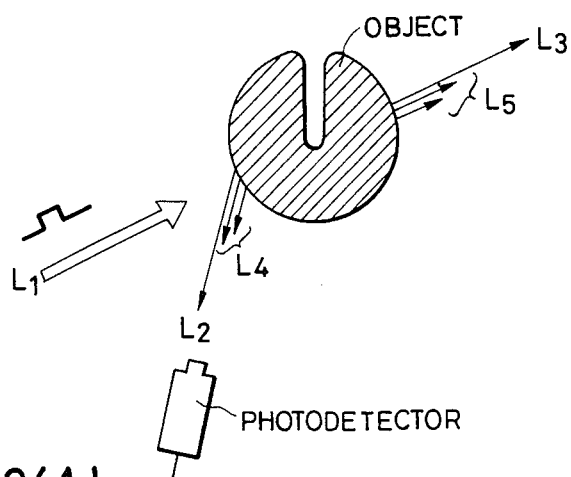
FIG. 1 is a block diagram illustrating the principle of the present invention.

FIG. 1 is a block diagram for explaining the principle of the invention. In FIG. 1, $L_1$ represents an incident light pulse (a probe light) to an object; $L_2$, a light pulse reflected from the surface of the object; $L_3$, a light pulse transmitted through the object; and $L_4$ and $L_5$, scattered light pulses which contain information on an inner structure of the object. The reflected light pulses comprising $L_2$ and $L_4$ contain information on the spatial depth of the object and scattering characteristics of the object, while the transmitted light pulses comprising $L_3$ and $L_5$ contain information on the transmissivity and index of refraction on the object.

When the light pulse $L_1$ is applied to the object, there are observed a flux of the reflected light pulses from and a flux of the transmitted light pulses through the object. The flux of the reflected light pulses comprises a light pulse $L_2$ reflected from the surface of the object and scattered light pulses $L_4$ reflected back from various parts having different indices from each other within the object. If a photodetector is disposed in the propagating direction of the reflected light pulses, the scattered light pulses are detected with their respective time delays after the light reflected from the surface of the object is detected because each of the scattered light pulses is delayed for a period when it is propagated within the object. Such a time-delay distribution of the scattered light pulses contains information on the surface shape and inner structure of the object. Also, the flux of the transmitted light pulses comprises a light pulse purely transmitted through the object and scattered light pulses propagating through the object with some scattering. Therefore, the inner structure of the object can be measured by analyzing the time-delay distribution of the scattered light pulses and the flux of the transmitted light pulses.

Figure 2A:
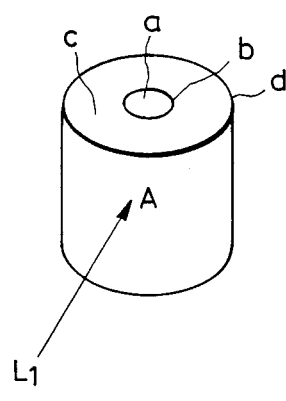
FIG. 2(A) illustrates an object to be three-dimensionally measured by the apparatus of the present invention and FIG. 2(B) is a top view of the object as shown in FIG. 2(A).

FIG. 2(A) is an illustration of the object to be measured for the purpose of understanding the principle of the invention more easily.

This object comprises a first cylinder (b) forming a hollow portion (a) therein and a second cylinder (d) surrounding the first cylinder (b), which form a hollow portion (c) therebetween and have different refractive indices from the hollow portions.

Figure 2B:
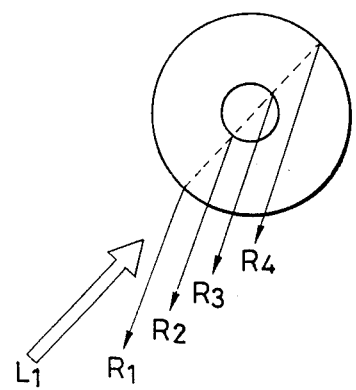

FIG. 2(B) is a top view of the object as shown in FIG. 2(A). When a light pulse $L_1$ is applied to a point A of the object, a flux of the reflected light pulses is detected by a photodetector. $R_1$ represents a light pulse reflected from the surface of the object and $R_2$, $R_3$, and $R_4$ represent scattered light pulses reflected from the interior of the object.

Figure 3:
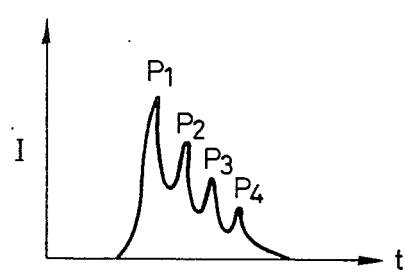
FIG. 3 shows an intensity distribution of light reflected from the object as a function of time.

FIG. 3 is a diagram showing the time-delay distribution of the intensity (I) of the flux of the reflected light pulses as a function of time. In FIG. 3, a peak $P_1$ is caused by the light pulse $R_1$; peaks $P_2$, $P_3$ and $P_4$, by the scattered (reflected) light pulses $R_2$, $R_3$ and $R_4$, respectively. The whole inner structure, that is, a three-dimensional surface shape and inner structure of the object can determined by shifting the incident position A of the light pulse to the object and measuring the time-delay distrubution at each position.

Any photodetector can be employed in the above measurement operation if it has the functions of measuring and analyzing three-dimensional information on time, space and intensity of a flux of reflected or transmitted light pulses, either simultaneously or with time and/or space division of the three-dimensional information. Some examples of apparatuses having the above functions are described hereinafter.

Figure 4:
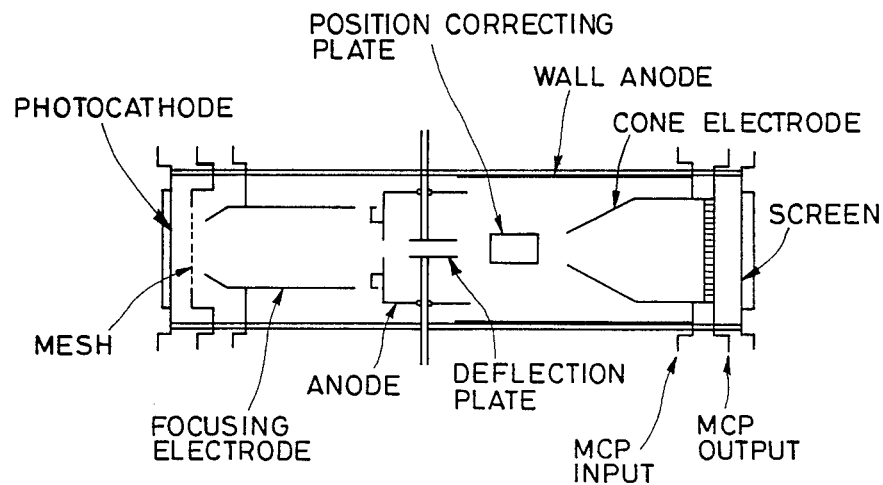
FIG. 4 shows the basic construction of a streak tube employed as ultrahigh speed light detecting means according to the present invention.

FIG. 4 shows a streak tube comprising a photocathode, a pair of deflecting plates for deflecting photoelectrons from the photocathode, and a phosphor screen for receiving the photoelectrons and forming a streak image thereon. The streak camera can simultaneously measure three-dimensional information of a light pulse, that is, the intensity distribution of the light with time and space with time resolution of the order of a picosecond to a subpicosecond.

Figure 5:
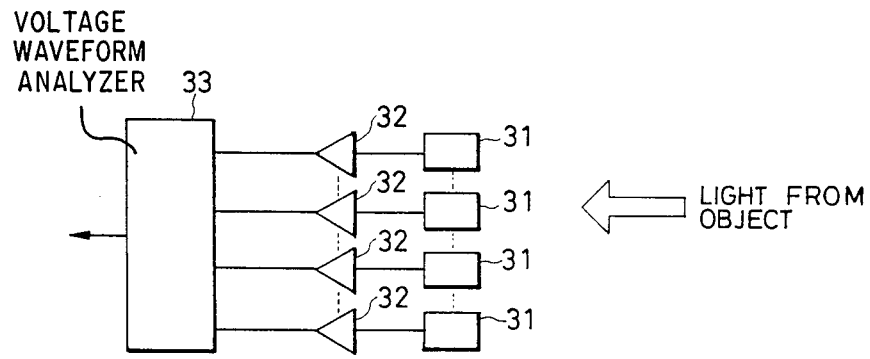
FIG. 5 shows an embodiment of the ultrahigh speed light detecting means according to the present invention.

FIG. 5 shows a second example of the ultrahigh speed light detecting means. This example comprises photodiodes 31 for detecting light pulses reflected from or transmitted through an object, amplifiers 32 electrically connected to the respective photodiodes for amplyfing the outputs of the photodiodes, and an ultrahigh speed voltage-waveform analyzer 33 such as a sampling oscilloscope which is electrically connected through the amplifiers to the photodiodes and which analyzes the voltage-waveforms of the outputs of the photodiodes. The photodiodes are set in an array and have rise times of the order of a picosecond. Accordingly, this apparatus can simultaneously measure three-dimensional information on the change of the intensity of the light pulses from the object with time and space with time resolution on the order of a picosecond. In place of the photodiodes, a multi-anode type of microchannel-plate (MCP) or a photomultiplier tube (PMT) having a multi-output portion may be used in this apparatus.

Each of the outputs from the photodiodes, the MCP and the PMT comprises a picosecond-order voltage-waveform having output power of the order of a mV. Accordingly, this apparatus can simultaneously measure three-dimensional information on time, space and the intensity of the light pulses from the object with time resolution higher than that of a presently manufactured MCP having a rise time of 150 picoseconds.

Figure 6:
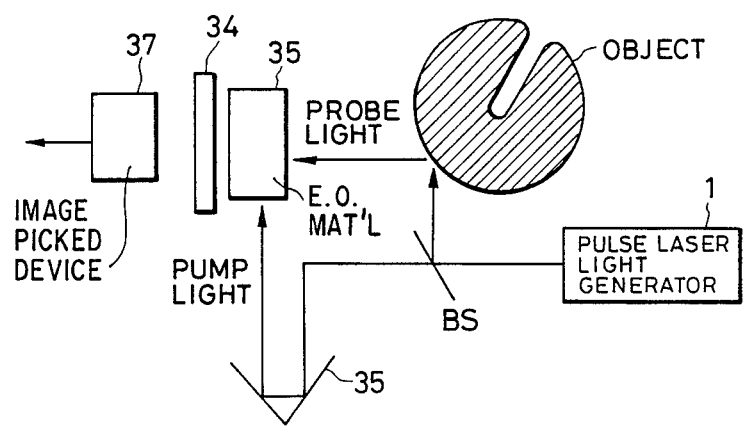
FIG. 6 is an explanatory diagram of a light detecting apparatus with a Kerr-shutter employed as the ultrahigh speed light detecting means.

FIG. 6 is an explanatory diagram of a light detecting apparatus with a Kerr-shutter capable of picosecond framing times.

The Kerr-shutter comprises an analyzer 34 and an electrooptic material 35, the optical rotation angle of which is changed by a pump light. The Kerr-shutter can be driven with picosecond framing times by use of a picosecond pump light. This apparatus adopts pulsed light from the pulse laser generator 1 as the pump light.

Pulsed light from the pulse laser generator 1 is split into two light pulses by a beam splitter (BS). One of the two light pulses is employed as a probe light for observing an object and the other is used as a pump light for driving the Kerr-shutter. Delaying means 36 for changing the timing of the Kerr-shutter is provided in the propagating direction of the pump light to slice the probe light from the object at an optional time. A sliced portion of the probe light is detected by an image picked device 37 such as a TV camera. The Kerr-shutter is repeatedly operated until all of the sliced portions are detected. All of the sliced portions thus obtained are analyzed with time resolution on the order of a picosecond, to thereby obtain three-dimensional information on time, space and the intensity of the probe light from the object. In this apparatus, the framing time of the Kerr-shutter is determined by a pulse width of a light pulse from the pulse laser generator and time response of the electrooptic material.

Figure 7:
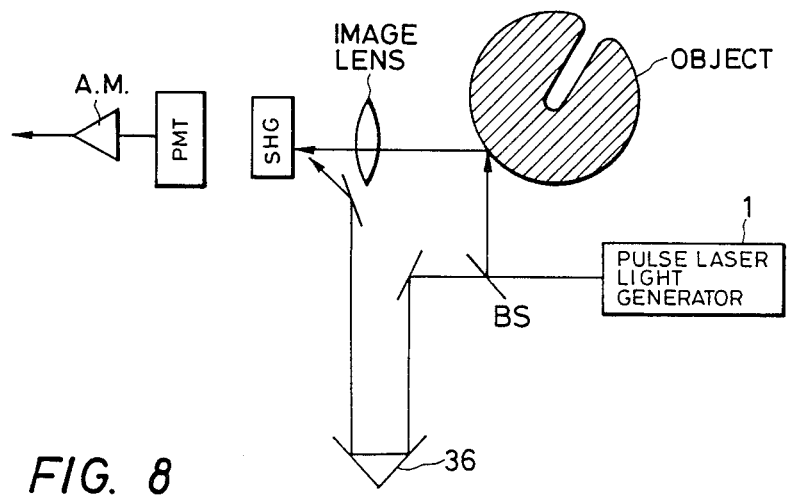
FIG. 7 is an explanatory diagram of an optical measuring apparatus adopting an auto-correlation method which is employed as the ultrahigh speed light detecting means according to the present invention.

FIG. 7 is an explanatory diagram of an optically measuring apparatus adopting an auto-correlation method, which is described in more detail in "OPTICS LETTER" 11(3), March 1986, by J. G. Fujimoto, S. De Silvestri, and E. P. Ippen.

This apparatus has the same construction as the above example described in connection with FIG. 6, except that the Kerr-shutter and the image pickup device are replaced by a second-harmonic generator (SHG) and a photomultiplier tube (PMT). The SHG comprises a nonlinear crystal for generating a second harmonic of an incident light pulse. In this case, a light pulse (a probe light) from an object and a light pulse delayed for a period by a delaying means are superimposed on each other within the SHG. As the intensity of the second harmonic from the SHG depends on the extent of the superimposition of the two light pulses from the object and the delaying means, the intensity distribution of the probe light with time is obtained by measuring the change of the intensity of the second harmonic with time. Space information is obtained by shifting an image lens or the object. Accordingly, three-dimensional information on time, space and the intensity of the probe light can be measured.

The image lens and the PMT may be replaced by a cylindrical lens and one-dimensionally arrayed photodetecting elements such as photodiodes in order to omit the shifting operation of the image lens or the object and simultaneously obtain three-dimensional information on time, space and the intensity of the probe light. This apparatus can measure the three-dimensional information in the order of a femtosecond by use of a femtosecond laser pulse.

The following embodiments are described in the case where a streak camera is employed as the ultrahigh speed light detecting means. Other apparatuses having the same function as the streak camera can be employed.

Figure 8:
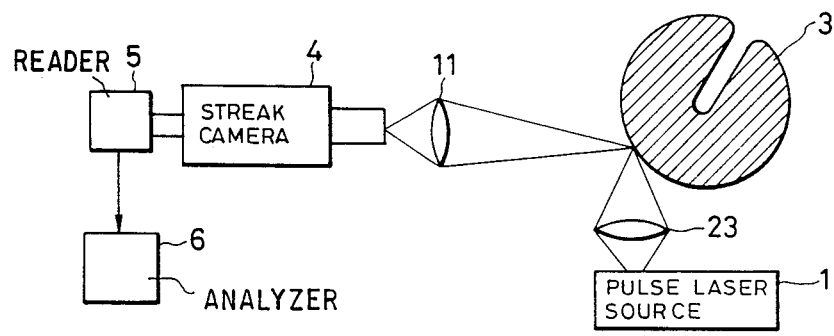
FIG. 8 is a block diagram showing a first embodiment of the three-dimensionally measuring apparatus according to the present invention.

FIG. 8 is a block diagram showing a first embodiment of the apparatus for three-dimensional measurement of the surface shape and inner structure of an object to be measured.

This embodiment is constructed so that three-dimensional measurement of the surface shape and inner structure of the object is attained in such a manner that a light pulse is applied to the object and detected after being reflected from the object. A pulse laser light source 1 is arranged to generate pulsed light having a short pulse width and comprises a light source such as an YAG laser, a gas laser, a dye laser, a semiconductor laser, or the like, in which short pulse generation is made by mode-locking. A streak camera 4 comprises a streak tube for high speed detection. The streak tube as shown in FIG. 4 is formed by providing an electron deflection electrode within a converging electron lens of an image tube. A deflection voltage (for signal sweeping) is applied to the electrode.

This embodiment is used for measuring a whole three-dimensional surface shape and inner structure of a living body or the like as the object 3.

The pulsed light reflected from the object 3 is focused onto a photocathode of the streak tube of the streak camera 4. The streak image read by a reader 5 is analyzed by an analyzer 6 so as to attain a three-dimensional data analysis of the interior of the object 3. If a scan means (not shown) is disposed between the pulse laser generator 1 and the object 3 to scan the object, the whole surface shape and inner structure of the three-dimensional object can be measured.

Figure 9:
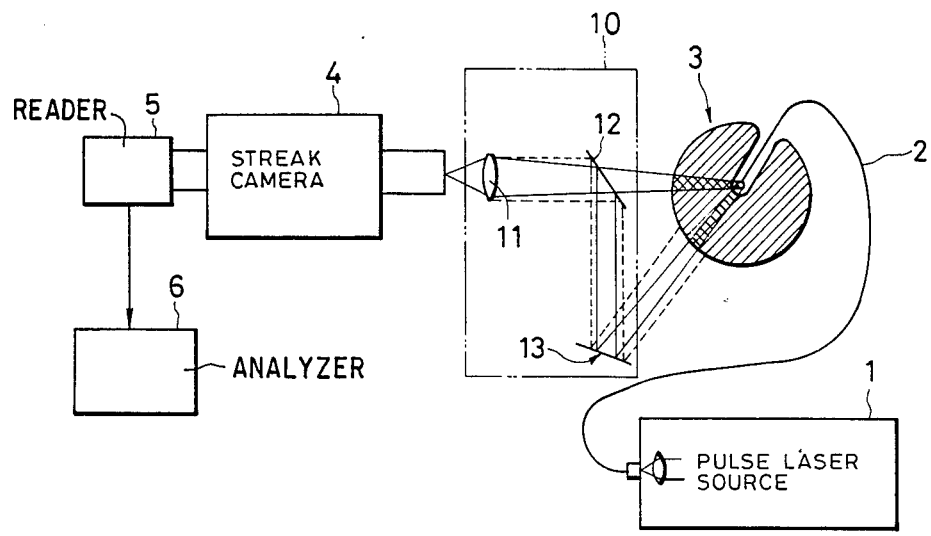
FIG. 9 is a block diagram showing a second embodiment of the three-dimensionally measuring apparatus according to the present invention.

FIG. 9 is a block diagram showing a second embodiment of the apparatus for three-dimensional measurement of an inner structure of an object to be measured, according to a second aspect of the present invention.

This embodiment is constructed so that three-dimensional measurement of the inner structure of the object is attained in such a manner that a light pulse is inserted into the object through an optical fiber and detected after being transmitted through the object.

The optical fiber 2 is arranged to guide the light pulse from the pulse laser light source 1 into the inside of the object 3 to be measured and to make the light pulse radiate at a suitable steroscopic angle.

This embodiment is used for measuring internal organs of a living body or the like.

The light pulse transmitted to the outside from the inside of the object 3 after being radiated from the optical fiber 2 is focused onto a photocathode of the streak tube of the streak camera 4 through a transmitted light focusing optical system 10.

The transmitted light focusing optical system 10 is constituted by a half mirror 12, a total reflection mirror 13 and a lens 11. In this embodiment, two images, one formed by the half mirror 12 and the lens 11, and the other formed by the total reflection mirror 13, the half mirror 12 and the lens 11, are analyzed.

The streak image read by a reader 5 is analyzed by an analyzer 6 so as to attain three-dimensional data analysis for the interior of the object 3.

In this embodiment, the pulsed light radiated from the end of the optical fiber 2 located inside the object 3 is a spherical wave.

Accordingly, the temporally-resolved image of the streak camera 4 appears as an image formed by superimposing modulation due to the inner structure of the object 3 on the spherical wave light pulse image.

When the curvature of the spherical wave light radiated from the optical fiber 2 is removed from the streak image on the basis of a preliminary calculation of the curvature by the analyzer 6, the inner structure of the object is revealed.

Although FIG. 9 shows the case where the transmitted light image in two directions of the object 3 is analyzed through the streak camera 4 including a converging lens, an optical structure may be arranged at the output end of the fiber to spread light in all 4 directions to thereby make it possible to analyze light transmitted through the object in any direction.

Figure 10:
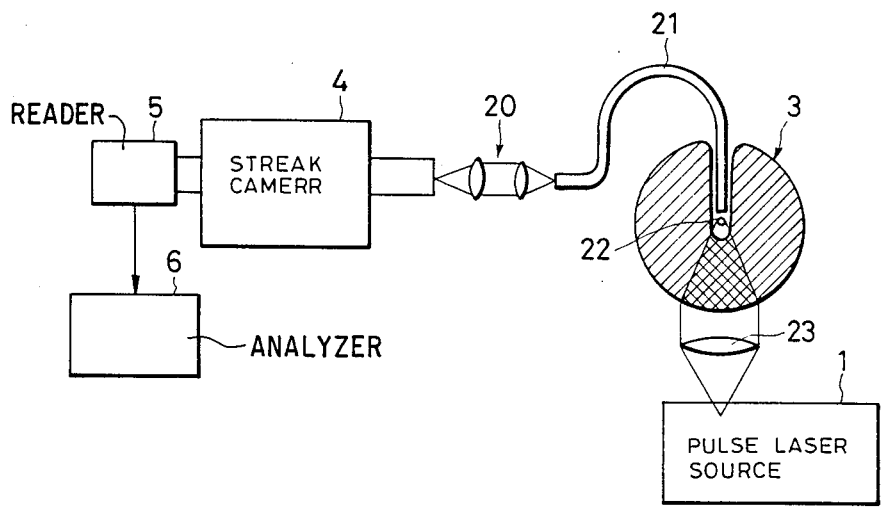
FIG. 10 is a block diagram showing a third embodiment of the three-dimensionally measuring apparatus according to the present invention.

FIG. 10 is a block diagram showing a third embodiment of the optical apparatus for three-dimensional measurement of the inner structure of an object to be measured according to the present invention.

A light pulse of a short pulse width from a pulse laser light source 1 is radiated through a lens 23 from the outside to the inside of an object 3 to be measured. An optical image fiber for guiding the image of the light pulse transmitted through the object 3 is inserted into the object 3. An objective lens 22 is provided at a top end of the optical image fiber 21 to obtain information of a certain region of the inside of the object 3. An output image of the image fiber 21 is focused onto a photocathode of a streak tube of a streak camera 4 through an optical system 20 composed of two lenses. An output of the streak camera 4 is read by a reader 5 and analyzed by an analyzer 6 to thereby attain a three-dimensional data analysis of the inside of the object 3.

This embodiment has an advantage in that, when the light absorption of the object is so large as to significantly reduce the light quantity transmitted through the object, the detected light quantity can be increased by detecting the transmitted light at the inside of the object 3 to thereby improve the S/N ratio.

Figure 11:
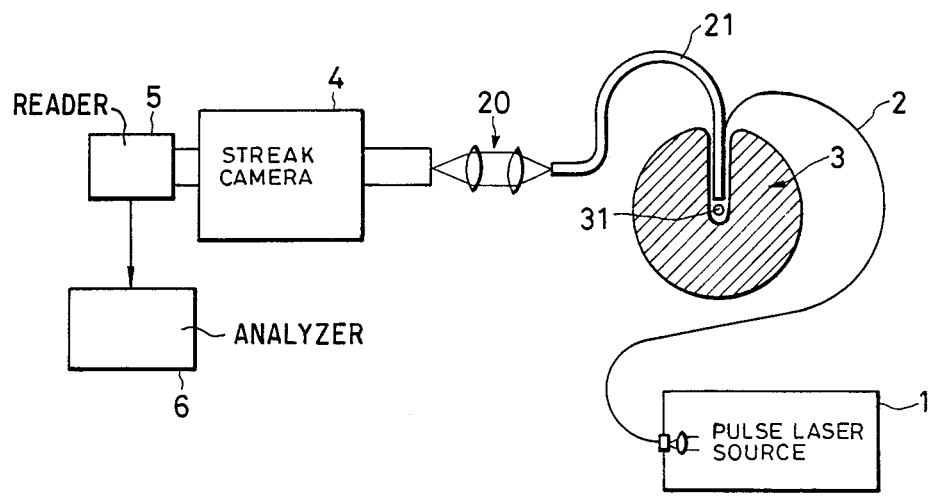
FIG. 11 is a block diagram showing a fourth embodiment of the three-dimensionally measuring apparatus according to the present invention.

FIG. 11 is a block diagram showing a fourth embodiment of the optical apparatus for three-dimensional measurement of an inner structure of an object to be measured, according to the present invention.

This embodiment is constructed so that the measurement is attained in such a manner that pulsed light is guided into the object through an optical fiber, and an image of light reflected from the inside of the object is detected through an image guide inserted into the object.

A light pulse having a short pulse width from a pulse laser light source 1 is inserted into an object 3 to be measured through an optical fiber 2 and radiated into the inside of the object 3 through a lens 31.

An end of an optical image fiber 21 is inserted into the object 3. The image of light projected into the object through the optical fiber and reflected at the inside of the object is fed through the optical image fiber 21.

The light projected into the object is reflected back from various areas of the object with reflection indicis different from each other. Light reflected from peripheral parts of the object is delayed more than light reflected from closer portions of the object.

The output of the streak camera 4 is read by a reader 5 and analyzed by an analyzer 6 to thereby attain three-dimensional data analysis of the inside of the object 3.

According to the aforementioned apparatus, the three-dimensional shape of the inside surface of the object and the inner structure of the surface area can be revealed.

This apparatus is useful in the case where the detailed inner structure or the like of an object of low light transmittance must be revealed.

Figure 12:
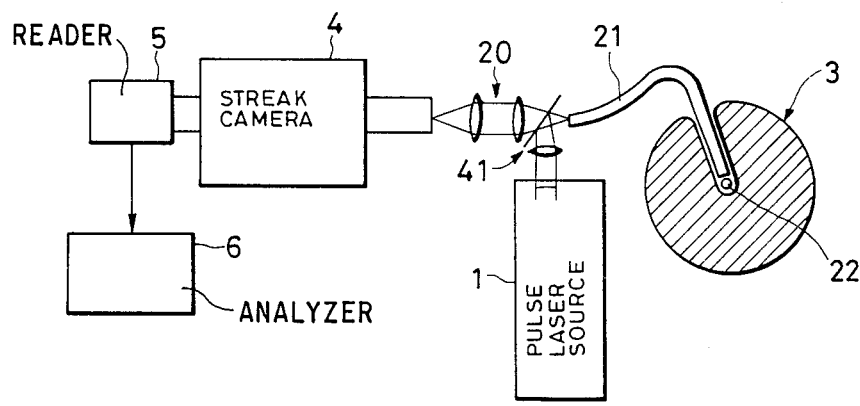
FIG. 12 is a block diagram showing a fifth embodiment of the three-dimensionally measuring apparatus according to the present invention.

FIG. 12 is a block diagram showing a fifth embodiment of the optical apparatus for the three-dimensional measurement of the surface shape and inside structure of an object to be measured, according to the present invention.

This apparatus is constructed so that the measurement is attained in such a manner that pulsed light is guided into the object through an image guide, and an image of light reflected from the inside of the object is detected through the image guide.

A light pulse of a short pulse width from a pulse laser light source 1 is reflected by a half mirror 41 and fed into an end of an optical image fiber 21 with the other end thereof inserted into the inside of an object 3 to be measured, so that the inside of the object is irradiated with the light.

The light projected into the object is reflected back from various parts scattered within the object with reflection indicis different from each other. Light reflected by a distant part is delayed more.

The image of light from the image fiber 21 is focused by a converging optical system 20 onto a photocathode of a streak tube of a streak camera 4.

The output of the streak camera 4 is read by a reader 5 and analyzed by an analyzer 6 to thereby attain three-dimensional data analysis of the inside of the object 3.

According to this apparatus, the three-dimensional shape of the surface of the object and the inner structure of the surface area can be revealed in the same manner as the apparatus shown in FIG. 11. This apparatus is useful in the case where the detailed inner structure or the like of an object of low light transmittance must be revealed.

As described above, according to the present invention, the three-dimensional shape and inner structure of a three-dimensional object can be measured by detecting and analyzing light pulses reflected from or transmitted through the object.

Further, when the abdomen of a human body is used as the object to be measured, both the light absorption and thickness of which are considerable so that a large quantity of incident light is required to obtain light transmitted through the abdomen, the rate of light detection can be greatly improved with no consideration except the influence of light absorption due to the walls of the abdomen or stomach. This is achieved because a very small and strong optical fiber can be used for guiding short light pulses into a living body to detect transmitted light pulses from the inside of the object at the outside of the body or an image fiber (endoscope) is inserted into the living body to detect the transmitted light pulses from the outside of the body.

Not only can the apparatus according to the present invention be used for the measurement of a living body such as a human body or the like, but also it can be widely used for the measurement of the surface shape and inner structure of manufactured articles.

The apparatus according to the present invention can employ a light in the range of the infrared region to the X-ray region as the incident (probe) light on an object.

What is claimed is:

1. An apparatus for optically measuring a three-dimensional surface shape and inner structure of an object, comprising:
   a pulse light source for generating pulsed light having a first pulse width;
   light conducting means for guiding said pulsed light from said pulse light source to said object;
   light detecting means for detecting one of a flux of reflected light pulses from a flux of transmitted light pulses through said object and measuring the change of the intensity of said one flux with respect to time and space, each of said flux of reflected light pulses and flux of transmitted light pulses having a time-delay distribution; and analyzing means for analyzing outputs of said ultrahigh speed light detecting means.

2. An apparatus as claimed in claim 1, wherein said light conducting means comprises an optical fiber, one end of said optical fiber being inserted into the inside of said object to guide said pulsed light into said object.

3. An apparatus as claimed in claim 2, said apparatus further comprising an optical system for focusing light pulses transmitted through said object onto an input portion of said ultrahigh speed light detecting means.

4. An apparatus as claimed in claim 2, further comprising an optical image fiber having one end thereof inserted into the inside of said object, said flux of reflected light pulses being fed from the inside of said object by the optical image fiber and transmitted to said ultrahigh speed light detecting means.

5. An apparatus as claimed in claim 4, said apparatus further comprising an optical system for focusing the output of said optical image fiber onto an input portion of said ultrahigh speed light detecting means.

6. An apparatus as claimed in claim 1, wherein said light conducting means comprises a first optical system for irradiating said object with said pulsed light from said pulse light source.

7. An apparatus as claimed in claim 6, said apparatus further comprising a second optical system for focusing said flux of reflected light pulses from said object onto an input portion of said ultrahigh speed light detecting means.

8. An apparatus as claimed in claim 6, said apparatus further comprising an optical image fiber having one end thereof inserted into the inside of said object, said flux of transmitted light pulses being fed from the outside to the inside of said object by said optical image fiber.

9. An apparatus as claimed in claim 8, said apparatus further comprising a second optical system for focusing the output of said optical image fiber onto an input portion of said ultrahigh speed light detecting means.

10. An apparatus as claimed in claim 1, wherein said light conducting means comprises an optical image fiber having one end thereof inserted into the inside of said object, said optical image fiber guiding said pulsed light to said inside and transmitting an image of said flux of reflected light pulses from inside said object to said ultrahigh speed light detecting means.

11. An apparatus as claimed in claim 10, said apparatus further comprising an optical system for focusing the output of said optical image fiber onto an input portion of said ultrahigh speed light detecting means.

12. An apparatus as claimed in claim 1, wherein said ultrahigh speed light detecting means comprises a streak camera comprising a streak tube including a photocathode, a deflecting plate for deflecting photoelectrons from said photocathode and a phosphor screen for receiving said deflected photoelectrons and forming a streak image thereon.

13. An apparatus as claimed in claim 1, wherein said ultrahigh speed light detecting means comprises a photodetector means having a rise time on the order of several tens of picoseconds to several hundred picoseconds for receiving said one flux and converting said one flux into electric signals. amplifiers electrically connected to said photodetector for amplifying said electric signals; and a high-speed voltage-waveform analyzer for analyzing respective voltage-waveforms of said electric signals from said amplifiers.

14. An apparatus as claimed in claim 13, wherein said photodetector means comprises an array of photodiodes.

15. An apparatus as claimed in claim 13, wherein said photodetector means comprises a micro-channel-plate having a multi-output type multi anode portion.

16. An apparatus as claimed in claim 1, wherein said ultrahigh speed light detecting means comprises a Kerr-shutter for passing said one flux from said object during the effectuation of said Kerr-shutter, an image pickup device having two-dimensional image pickup elements for detecting said one flux passed through said Kerr-shutter, and delaying means, disposed between said pulse light source and said Kerr-shutter, for delaying a light pulse from said pulse light source and supplying it to said Kerr-shutter as a pump light, said Kerr-shutter being driven by irradiation from said pump light.

17. An apparatus as claimed in claim 1, wherein said ultrahigh speed light detecting means comprises a second harmonic generator for receiving said one flux from said object and generating a second harmonic of said one flux;

a photomultiplier tube (PMT) for detecting said second harmonic from said second harmonic generator; and delaying means, disposed between said pulse light source and said harmonic generator, for delaying a light pulse from said pulse light source and supplying it to said second harmonic generator, the intensity of said second harmonic depending on the extent of the superimposition of said one flux and said delayed light pulse from said pulse light source.

* * * * *

UNITED STATES PATENT AND TRADEMARK OFFICE
CERTIFICATE OF CORRECTION

PATENT NO. : 4,857,748
DATED : August 15, 1989
INVENTOR(S) : Yoshihiro Takiguchi It is certified that error appears in the above-identified patent and that said Letters Patent is hereby corrected as shown below:

Claim 1, column 8, line 63, "from" should be followed by --and--.

Claim 13, column 10, line 13, change "." to --,--.

Signed and Sealed this

Tenth Day of December, 1991

*Attest:*

HARRY F. MANBECK, JR.

*Attesting Officer*   *Commissioner of Patents and Trademarks*